(12) United States Patent
Koch et al.

(10) Patent No.: US 11,131,585 B2
(45) Date of Patent: Sep. 28, 2021

(54) PROCESS FOR THE CONTACTLESS DETERMINATION OF THE SKIN TEMPERATURE AND DEVICE FOR CARRYING OUT THE PROCESS

(71) Applicant: Drägerwerk AG & Co. KGaA, Lübeck (DE)

(72) Inventors: Jochim Koch, Ratzeburg (DE); Jasper Diesel, Lübeck (DE); Marc-Florian Uth, Hamburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 437 days.

(21) Appl. No.: 16/194,812

(22) Filed: Nov. 19, 2018

(65) Prior Publication Data
US 2019/0154509 A1    May 23, 2019

(30) Foreign Application Priority Data
Nov. 22, 2017    (DE) ..................... 10 2017 010 801.3

(51) Int. Cl.
| | |
|---|---|
| *G01J 5/00* | (2006.01) |
| *G01J 5/02* | (2006.01) |
| *A61B 5/01* | (2006.01) |
| *A61B 5/00* | (2006.01) |
| *G01K 13/20* | (2021.01) |
| *G01J 5/08* | (2006.01) |

(Continued)

(52) U.S. Cl.
CPC .......... *G01J 5/0025* (2013.01); *A61B 5/0075* (2013.01); *A61B 5/01* (2013.01); *A61B 5/015* (2013.01); *G01J 5/026* (2013.01); *G01J 5/089* (2013.01); *G01K 13/223* (2021.01); *H04N 5/33* (2013.01); *A61B 2503/04* (2013.01); *G01J 5/522* (2013.01); *G01J 2005/0077* (2013.01)

(58) Field of Classification Search
USPC .......... 600/473, 474; 374/121; 702/135, 136
See application file for complete search history.

(56) References Cited

U.S. PATENT DOCUMENTS

| | | |
|---|---|---|
| 5,316,542 A | 5/1994 | Koch et al. |
| 6,048,304 A | 4/2000 | Koch |

(Continued)

FOREIGN PATENT DOCUMENTS

| | | |
|---|---|---|
| CN | 1939215 A | 4/2007 |
| CN | 107007267 A | 8/2017 |

(Continued)

*Primary Examiner* — Lisa M Caputo
*Assistant Examiner* — Nasir U. Ahmed
(74) *Attorney, Agent, or Firm* — McGlew and Tuttle, P.C.

(57) ABSTRACT

A process and a device are provided for a contactless determination of a measuring location (32) on a body, which point is intended for the measurement of a skin temperature of a human being (10). A signature (36) indicating a measuring location (32) on the body is detected by means of a sensor system (16). A skin temperature measurement is carried out on the measuring location (32) on the body. A signature (36) detectable in the infrared range and a sensor system (16) sensitive in the infrared range are used. Both the detection of the infrared range signature (36) and the measurement of the skin temperature at the measuring location (32) on the body are carried out by means of the sensor system (16) sensitive in the infrared range.

20 Claims, 6 Drawing Sheets

(51) Int. Cl.
*H04N 5/33* (2006.01)
*G01J 5/52* (2006.01)

(56) References Cited

U.S. PATENT DOCUMENTS

| | | | |
|---|---|---|---|
| 6,409,653 B1 | 6/2002 | Koch et al. | |
| 7,292,719 B2* | 11/2007 | Arnon | A61B 5/015 128/922 |
| 7,364,356 B2* | 4/2008 | Dicks | A61B 5/01 374/121 |
| 8,620,041 B2* | 12/2013 | Arnon | G06T 7/0012 382/128 |
| 8,831,295 B2 | 9/2014 | Coons | |
| 9,098,908 B2 | 8/2015 | Kirk et al. | |
| 9,823,755 B2 | 11/2017 | Zhang et al. | |
| 9,993,733 B2 | 6/2018 | Athavale et al. | |
| 2008/0071189 A1 | 3/2008 | Yarden et al. | |
| 2011/0298204 A1* | 12/2011 | Eschbach | B42D 25/29 283/67 |
| 2012/0316425 A1* | 12/2012 | Raleigh | A61B 6/584 600/411 |
| 2013/0342691 A1 | 12/2013 | Lewis et al. | |
| 2015/0001189 A1 | 1/2015 | Spinella et al. | |
| 2016/0223731 A1* | 8/2016 | Free | G02B 5/305 |
| 2018/0004355 A1 | 1/2018 | Shahar et al. | |
| 2018/0249095 A1 | 8/2018 | Lee et al. | |

FOREIGN PATENT DOCUMENTS

| | | |
|---|---|---|
| DE | 17 95 942 U | 9/1959 |
| DE | 10 2005 049 676 B3 | 11/2006 |
| DE | 10 2015 009 088 A1 | 1/2017 |
| JP | H05-180699 A | 7/1993 |
| JP | H11-169363 A | 6/1999 |
| JP | 2005-287806 A | 10/2005 |
| JP | 2007-151686 A | 6/2007 |
| JP | 2011-254847 A | 12/2011 |
| WO | 2009/083974 A | 7/2009 |

* cited by examiner

PROCESS FOR THE CONTACTLESS DETERMINATION OF THE SKIN TEMPERATURE AND DEVICE FOR CARRYING OUT THE PROCESS

CROSS REFERENCE TO RELATED APPLICATIONS

This application claims the benefit of priority under 35 U.S.C. § 119 of German Application 10 2017 010 801.3, filed Nov. 22, 2017, the entire contents of which are incorporated herein by reference.

TECHNICAL FIELD

The present invention pertains to a process for the contactless determination of the skin temperature of a patient, especially of a newborn or of an infant, and generally to a process for the contactless determination of the skin temperature of a human being. For the sake of better readability of the following description, it will be continued below based on the example of a process for the contactless determination of the skin temperature of a patient. A process for the contactless determination of the skin temperature of a newborn or of an infant as well as generally a process for the contactless determination of the skin temperature of a human being shall always be implied.

BACKGROUND

The skin temperature measurement and regulation of newborns in incubators and regulation, by means of, for example, radiation type heating units has already been employed for several decades. With the patient in the supine position, a skin temperature sensor is placed over the abdomen (liver), and it is placed over the kidney if the patient is in the prone position. A set point, for example, 36.5° C., is preset for the skin temperature regulators, and the air temperature in the incubator is adapted by means of the regulator, so that the set point is reached as a skin temperature measured value after a certain adaptation time (ranging from several minutes to about 30 minutes). The skin temperature shall thus be maintained at a stable level. The temperature regulation facilitates the operation of the thermotherapy devices for the health care staff and reduces the effort needed for monitoring. The set point of the skin temperature is maintained in radiation type heating units directly by regulating the output of the heat radiator.

However, the regulation of the skin temperature is not limited to certain regions of the body. Rather, regions other than those mentioned may also be used for the regulation, for example, the forehead or the crown of the head of the patient. These regions are also related in some way thermally to the body core temperature.

A classical skin temperature sensor has hitherto been attached to the skin with an adhesive pad and connected to the temperature regulator with a cable. Adhesive bonding of the sensors is not popular among health care staff because the adhesive bond is not always reliable and the sensor may fall off. There is no reliable alarm at present for alerting to the sensor having fallen off. Furthermore, the adhesive of the adhesive pad may cause skin irritations and, especially in case of high humidity in the incubator, lose its adhesive effect. Moreover, the connection cable is disturbing during the care for the patient and during the handling of the patient. This is especially true in case of the so-called kangarooing, when parents take the newborn out of the incubator and place the newborn on their upper body.

An improvement of the current conditions can be achieved if the skin temperature is detected in a contactless manner.

A process for the contactless determination of the body temperature of a patient is known from DE 10 2015 009 088 A1. The entire body surface of the patient is detected in this case by means of an infrared camera. In addition, the surface of a heatable calibrating device placed in the detection area of the infrared camera is detected. The temperature of the calibrating device is adjusted until the detected radiation output of the calibrating device corresponds to the radiation output of the body surface, which output is detected by means of the infrared camera. The temperature to which the calibrating device was heated is then the patient's skin temperature to be detected.

While a measuring surface of the patient, which is relevant for the determination of the skin temperature, is assumed in DE 10 2015 009 088 A1 to be located in a detection area of the infrared camera, provisions are made in DE 10 2005 049 676 (corresponding to U.S. Pat. No. 7,364,356 B2, which is incorporated herein by reference in its entirety) for placing an orientation field on the measured body region of the patient. The orientation field is detected by means of a scanner and a temperature sensor unit with infrared sensors is directed towards the orientation field. The orientation field offers the possibility of optically identifying a fixed point on the body of the patient. The identification may be carried out, for example, by means of a web camera.

SUMMARY OF THE INVENTION

One object of the present invention is to provide an improved possibility for the contactless determination of the body temperature of a human being.

This object is accomplished according to the present invention by means of a process for the contactless determination of a measuring point (measuring location) on the body, which point is intended for the measurement of a skin temperature of a human being, as well as for the subsequent measurement of the skin temperature. Provisions are made in such a process for detecting a signature (characteristic indicator—a characteristic IR intensity distribution) indicating a measuring location on the body by means of a sensor system and for carrying out the skin temperature measurement on the measuring location on the body. The process is characterized in that a sensor system sensitive in the infrared range is used and a signature detectable in the infrared range (by different emissivities) is detected, and that both the detection of the signature and the measurement of the skin temperature on the measuring location on the body are carried out by means of the sensor system sensitive in the infrared range.

The signature is provided by a signature carrier applied to the body and provides an indication, in an infrared digital image, from a region of the body including the signature carrier. The indication (the signature) is provided by the signature carrier or by the signature carrier and the body to produce the signature in an infrared digital image. The signature comprises areas with different emission, transmission and/or reflection characteristics in the infrared range. The signature carrier provides the signature to indicate the measuring location. The measuring location can be indicated with a feature of the signature carrier, including a reflective element, a change in material, a hole in the material. The signature may define the measuring location or point to the measuring location. The position of the signature may be used to determine the position of the measuring location based on further information from data in a data base that relates the signature position to a predetermined measuring location. The advantage of the solution according to the present invention is that the detection of the signature and also the subsequent measurement of the skin temperature on the measuring location on the body, which is marked by means of the signature, are carried out by means of one and the same sensor system, namely, by means of the sensor system sensitive in the infrared range, especially by means of an infrared camera (IR camera). This guarantees a reduction in the amount of apparatus needed. A small and compact structural shape of a measuring device, which comprises the system sensitive in the infrared range, is thus made possible. Moreover, the reduction in the amount of apparatus needed reduces the cost of manufacturing such a measuring device and also reduces the maintenance and upkeep costs.

The following description continues on the basis of an infrared camera as a sensor system sensitive in the infrared range (these also include, for example, matrix sensors with an array of thermopiles, but only infrared cameras will be mentioned in the further description). A digital image with a matrix-shaped arrangement of pixels of the respective detection area can be recorded by means of an infrared camera in a manner known per se and a signature possibly comprised by the digital image can be detected in the digital image with image processing algorithms, by applying a pattern recognition/pattern matching algorithm that are, in principle, known per se.

The steps described below are provided in one embodiment of the process, and it is assumed that the signature carrier comprising the signature is placed first on the patient by the health care staff such that the signature is located in a location whose skin temperature shall be measured: A digital image is recorded. The recording of the digital image is carried out by means of an infrared camera comprising the sensor system sensitive in the infrared range. The digital image comprises the patient at least partially and the digital image always comprises the signature or the part of the signature that is "visible" for the infrared camera. The position of the signature is determined in the digital image, for example, in the form of the coordinates of a corner point of the signature or of the coordinates of the focal point of the signature in the coordinates (row, column) of the digital image. The determination of the position of the signature in the digital image is carried out by means of image processing algorithms known, in principle, per se, or by means of "machine learning." In the second case, marked exemplary images, on the basis of which the selected machine learning process is conditioned for finding the signature, are fed manually into the computer. Further, the position of an image area of the measuring location on the body is determined in the digital image. No image processing algorithms or the like are necessary for this at least in one special embodiment of the process. The determination of the position of an image area of the measuring location on the body—the measuring location image area—is rather carried out on the basis of data that are known in respect to the signature. Because the signature, especially a signature shape and signature size in the digital image, is known, the position of the measuring location image area in the digital image can be directly derived from the position of the signature in the digital image. Location information belonging to the signature is used for this. The location information may implicitly belong to the corresponding signature, for example, if it is found on the basis of the data that are known with respect to the signature that the measuring location image area is located in the center of the signature. The coordinates of the center of the signature in the digital image and hence finally the measuring location image area can then be determined on the basis of the determined position of the signature in the digital image and of a dimension of the signature in the digital image, which can likewise be determined. As an alternative, location information to be used to determine the measuring location image area can also belong to the signature in the form of coordinates (offset in the X direction; offset in the Y direction). The coordinates of the signal in the digital image and hence finally the measuring location image area are then determined on the basis of the determined position of the signature in the digital image as well as of the location information. The measuring location image area may be located within the limits of the signature or also outside the limits of the signature. The location information may optionally also comprise a datum, which codes the dimension of the measuring location image area. As soon as the coordinates of the measuring location image area in the recorded digital image are known, the skin temperature of the patient is determined by analyzing an intensity distribution in the infrared range of the pixels of the digital image, which are comprised by the measuring location image area. The skin temperature is determined, in principle, in a manner known per se, for example, on the basis of an intensity or intensity distribution determined in the measuring location image area, especially on the basis of an intensity or intensity distribution resulting from a thermographic measurement. In case of materials transparent for infrared radiation in the measuring location image area, the recorded surface temperature corresponds to the skin temperature. This may be closely correlated to the body core temperature.

For example, a cap worn by the patient or another article of clothing (for example, a onesie) comprises at least two area sections with different emission, transmission or reflection characteristics in the infrared range in a preferred embodiment of the process. The article of clothing comprises the signature in the sense that the article of clothing has, for example, sections with different emission characteristics or sections with different transmission characteristics or sections with different emission and/or transmission characteristics in the infrared range. The article of clothing is thus the origin of the signature when detecting the article of clothing by means of the infrared camera, so that the article of clothing can be said to generate the signature. The article of clothing is the carrier of the signature (signature carrier) as well as the origin of the signature (signature origin), the latter being true in the sense that the article of clothing generates the signature within the framework of a detection by means of an imaging process. The article of clothing thus comprises a signature carrier and the article of clothing is an example of a signature carrier/signature origin. The signature carrier defines a signature with a known shape and size and defines a measuring location with a predetermined position relative to the signature. For the sake of better readability of the following description, the description will be continued on the basis of a cap as a signature carrier/signature origin. Whenever a cap is mentioned, other articles of clothing, for example, a onesie, shall always be implied. Another example of a signature carrier/signature origin is a film applied detachably to the skin of the patient, which comprises/generates the signature, especially a film stuck on the skin of the patient.

Two such area sections are obtained, for example, when the signature carrier—the cap or the article of clothing in question—has an opening without textile fabric or the like, i.e., more or less a "hole" (transmittance >>0). The opening is an area section with a first emission and transmission characteristic in the infrared range. Areas of the signature carrier adjoining the opening have a second emission and transmission characteristic in the infrared range that is different from the first emission and transmission characteristic in the infrared range (in the area of the opening). The area of the opening is preferably used for the skin temperature measurement and the signature carrier is consequently placed with the position of signature such that the opening is located on the measuring location on the body.

A signature carrier generally comprises a signature such that this signature carrier comprises areas with different emission, transmission and/or reflection characteristics in the infrared range and these areas are distributed in a characteristic manner over the signature carrier. The distribution of such areas having different emissions, transmissions and/or reflections in the infrared range may lead, for example, to a checkered distribution and correspondingly to a checkered signature. As an alternative, a signature may be provided on the signature carrier in the form of concentric rings. Any other distribution of such areas having different emissions, transmissions and/or reflections in the infrared range is likewise advantageous and shall be considered to be covered by the description being presented here with this reference. Precisely the fact that any desired local distribution of areas having different emissions, transmissions and/or reflections in the infrared range may be provided, in principle, is the linkage point for the distinguishability of different signatures and hence also the linkage point for an automatic distinguishability of different signatures according to a special variant of the principle being proposed here. The signature is inherently contained in the respective signature carrier, i.e., for example, the cap or the film defines a signature with a known shape and size and defines a measuring location with a predetermined position relative to the signature. The signature appears optically perceptibly and in an automatically analyzable form as an image within the framework of a photographic image (by means of an infrared camera or a thermography camera) of a scene, which comprises at least the signature carrier or a part of the signature carrier.

A signature carrier in the form of a cap or of a film is well suited for use in clinical practice and interferes at most minimally with other necessary clinical and/or therapeutic actions. Moreover, such a cap or film is hardly disturbing for the patient and is usually used in the case of ventilated patients anyway to fix the ventilation tube.

Provisions are made in one embodiment of the process for the skin temperature measurement and/or the analysis of the measuring location image area, especially a processing of a sensor signal, which is generated during the skin temperature measurement and codes an indicator for the measured temperature, to be carried out as a function of a particular detected signature. This makes it possible to mark different body regions of the patient with a respective characteristic signature. Based on the particular signature detected, it can then automatically be recognized whether the sensor systems detects, for example, the head of the patient in the area of the forehead, on the temple or in the area of the crown of the head. Depending on the signature, i.e., depending on the body region/body section, a specific weighting and/or a specific algorithmic processing of the sensor signal can be carried out in order to obtain a reliable value for the skin temperature, for example, even in case of detection of a body region/body section which region or section is less suitable for the direct determination of the body temperature than, for example, the forehead area.

In a special embodiment of the variant of the process in which the skin temperature measurement and/or the analysis of the measuring location image area is carried out as a function of a particular detected signature, provisions are made for the signature carrier, i.e., for example, the cap or the film, to comprise/generate different signatures in different sections. Provisions may, for example, be made in the case of a cap for the cap to comprise/generate at least two of the following signatures: A signature in the region of the forehead ("forehead signature"), a signature in the region of the crown of the head ("crown signature"), one signature each on both sides in the region of the temples ("temple signature") and/or a signature in the occipital region ("occipital signature"). For example, different regions of the head of the patient can automatically be distinguished from one another by means of such a cap or another signature carrier. In case of a fixed position of the infrared camera, the position of the patient (supine position, lateral position, prone position) can thus be detected automatically at least approximately. Moreover, the region of the head in which the measurement of the skin temperature is carried out by means of the infrared camera can be automatically detected. It is possible, for example, to carry out a correction of the skin temperature measurement, which correction depends on the particular region of the head.

The possible signatures mentioned should expressly be considered to be examples only. A cap, as the signature carrier, may just as well comprise only one signature, i.e., for example, only one signature acting as a forehead signature. In addition, a region without locally different emission and/or transmission characteristics in the infrared range may even represent a signature of its own. The absence of a signature can automatically be detected in such a case and this can also be used for the automatic detection of the position of the patient and/or for the automatic processing of a temperature measured value. For example, processing of the generated sensor signal can be carried out in case of a measurement of the skin temperature in case the forehead signature is detected, and an auxiliary signal, which codes, for example, a reduced validity of the sensor signal, can be generated in addition to the sensor signal in a situation in which the forehead signature is not detected or no signature is detected at all, i.e., in which the infrared camera detects, for example, the temporal region or the back of the head of the patient.

A preferred embodiment of the variant of the process, in which the skin temperature measurement and/or the analysis of the measuring location image area is carried out as a function of a particular detected signature, comprises the following steps: The signature comprised by the digital image is first identified in the particular recorded digital image, especially by determining the position and the dimension of the signature in the digital image. The identified signature is then compared with at least one reference signature, optionally successively with a respective reference signature from a set of reference signatures. Moreover, machine learning processes with manually marked exemplary images can be conditioned such that the pixels in the image, which comprise the signature, can be marked with them. If a reference signature fitting the signature comprised by the recorded digital image could be identified, processing instructions or reference parameters linked with the respective reference signature are used when determining the skin temperature of the patient, for example, by analyzing the intensity distribution in the infrared range in the image area. For example, a numerical value (thermographic surface temperature measurement) proportional to the skin temperature on the measuring location on the body is obtained based on an analysis of, for example, the intensity distribution. This numerical value is weighted, for example, with the processing parameter corresponding to the processing instruction. This is an example of a possibility for a correction of the skin temperature measurement, which correction depends on a respective detected body region, especially a respective detected region of the head.

The above-mentioned object is also accomplished with a control unit for controlling a medical device or a medical treatment unit, which operates according to the process as here and hereinafter described, and comprises for this means for carrying out the process. The present invention is preferably implemented in software. The present invention also comprises a computer program with program code instructions executable by a computer, on the one hand, and, on the other hand, a storage medium with such a computer program, i.e., a computer program product with program code means, as well as finally also a control unit or a medical device or a medical treatment unit, in the memory of which device or unit such a computer program is or can be loaded as a means for carrying out the process and embodiments thereof.

Further, the present invention also comprises a treatment unit with means for carrying out the process as here and hereinafter described. Especially a sensor system sensitive in the infrared range, a processing unit in the form of or in the manner of a microprocessor as well as a control program that can be executed by means of the processing unit act as means for carrying out such a process.

The present invention also comprises a system with such a treatment unit and with an article of clothing acting as a signature carrier, which article of clothing comprises at least two area sections with different emission, transmission or reflection characteristics in the infrared range. An article of clothing in the form of a cap being worn by the patient with such area sections appearing differently in the infrared range preferably acts as a signature carrier.

Thus, the present invention is also such an article of clothing being worn by the patient, namely, for example, a cap, with at least two area sections having different emission, transmission or reflection characteristics in the infrared range, especially an article of clothing/a cap, which article of clothing or cap is intended for use as a signature carrier in a system according to the above paragraph and comprises for this at least two area sections with different emission, transmission or reflection characteristics in the infrared range. An article of clothing, especially a cap, with an opening—an IR window—is preferably used concerning the at least two area sections with different emission, transmission or reflection characteristics in the infrared range. Compared to the adjoining regions, the opening has a different emission, transmission or reflection characteristic in the infrared range. An image of the article of clothing can correspondingly be identified as a signature. The opening defines at the same time the measuring location on the body, because the skin of the patient is visible through the opening and the temperature measurement (contactless skin temperature determination) can thus be carried out on the measuring location on the body.

Finally, the present invention also comprises the use of an article of clothing according to the above paragraph, namely, the use of such an article of clothing as a signature carrier in a process of the type being here and hereinafter described.

An exemplary embodiment of the present invention will be explained in more detail below on the basis of the drawings. Mutually corresponding objects or elements are provided with the same reference numbers in all figures.

The exemplary embodiment or each exemplary embodiment shall not be considered to represent a limitation of the present invention. Variations and modifications, especially such variants and combinations which the person skilled in the art can find in view to accomplishing the object, for example, by combining or modifying individual features described in the general or special part of the description and/or contained in the drawings, and which lead to a new object through combinable features, are rather possible within the framework of the present disclosure.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
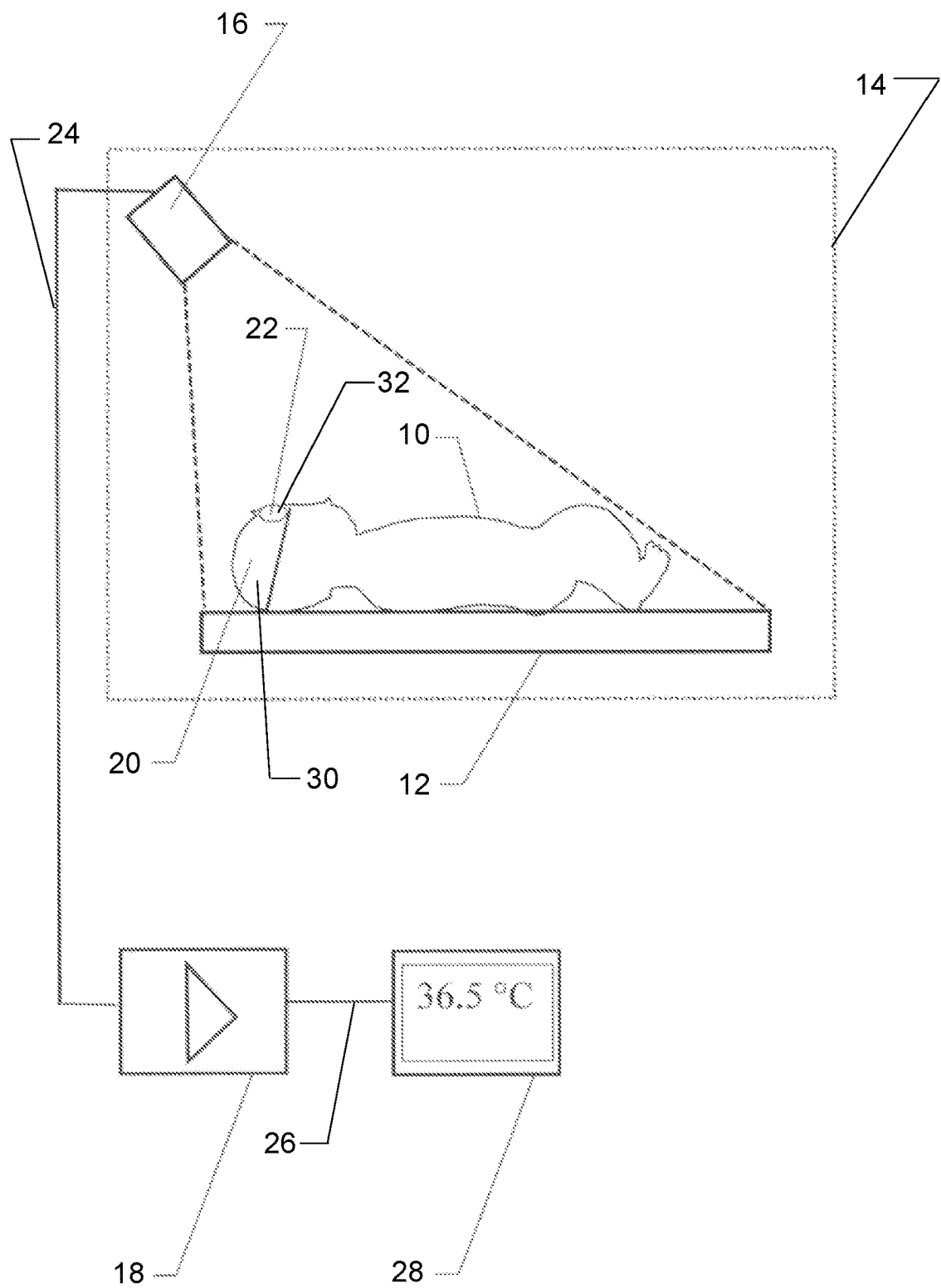
FIG. 1 is a schematic view showing a medical treatment unit with a patient and with an infrared camera arranged at the treatment unit for recording a digital image of the patient.

Referring to the drawings, the view in FIG. 1 shows in a schematically simplified manner a human patient 10 on a support 12, for example, a support 12 of a medical treatment unit 14 illustrated only by a boundary line. The treatment unit 14 is, for example, an incubator 14, which is known, in principle, per se. An infrared camera 16 is arranged at or in the treatment unit 14, especially stationarily in relation to the treatment unit 14 and with a fixed or fixable orientation. The infrared camera 16 is an example of a sensor system sensitive in the infrared range. The infrared camera 16 is connected to an analysis unit 18 or comprises such an analysis unit 18. The orientation of the infrared camera 16 is selected to be such that it fully or partially detects the patient 10. The detection range of the infrared camera 16 is illustrated by means of broken lines in the view shown in FIG. 1. The infrared camera 16 detects the patient 10 completely in the situation being shown.

The patient 10 is wearing a cap 20 in the configuration being shown. The cap 20 has at least one IR-transparent opening 22 (IR window 22) and/or generally an area section with an emission, transmission or reflection characteristic in the infrared range, which is different from that of another area section, thereby providing a signature, with the cap 20 comprising a signature carrier 30. In the interest of simple conditions, the further description will be continued on the basis of an IR-transparent opening 22.

Among other things, this opening 22 is also detected during the detection of a digital infrared image (FIG. 2) by means of the infrared camera 16, and the analysis of the infrared radiation in the area of the opening 22 makes it possible, in a manner that is known per se, in principle, such as performed by infrared thermometers, to determine a skin temperature of the patient 10. The digital image is processed for this by means of the analysis unit 18 by the image data recorded by means of the infrared camera 16 being transmitted via a data line 24 to the analysis unit 18 and being analyzed there. The analysis unit 18 sums up the values in a matrix of pixel values (pixel array) and compares this (an intensity or intensity distribution determined in the measuring location image area, especially on the basis of an intensity or intensity distribution resulting from a thermographic measurement) against one or more stored reference values. The analysis unit 18 generates a temperature signal 26, which is sent by the analysis unit 18, for example, to a display unit 28 and/or as a controlled variable for a regulator. The skin temperature of the patient 10 is finally displayed by means of the display unit 28 on the measuring location, namely, the skin temperature in the area of the IR window 22 is displayed.

The cap 20 being worn by the patient 10 on the head forms the signature carrier 30 in the example being shown. The IR window 22 defines a measuring location 32 on the body, i.e., a measuring location to which the determination of data for determining the skin temperature of the patient 10 pertains. The function of the cap 20 as a signature carrier 30 arises from the fact that the cap 20 or parts of the cap 20 causes/cause a characteristic intensity distribution—the signature 36—in the digital image 34 (FIG. 2) recorded by means of the infrared camera 16. This is shown in FIG. 2 in a schematically simplified manner.

Figure 2:
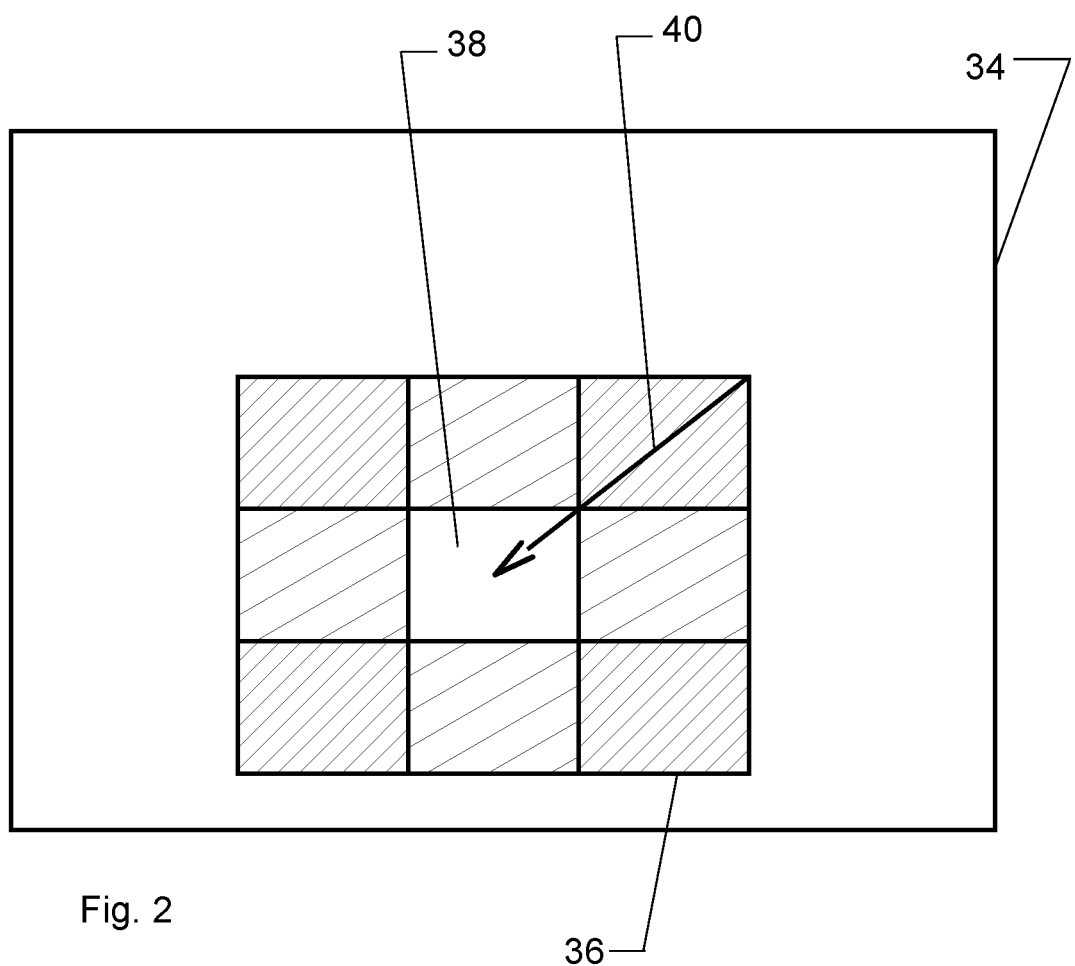
FIG. 2 is a schematic view showing a signature detected during the recording of a digital image of a patient.

The view in FIG. 2 shows in a schematically highly simplified manner a detail of a digital image 34 recorded by means of the infrared camera 16. The digital image 34 comprises a signature 36 resulting from a signature carrier 30 (for example, the cap 20) located in the detection area of the infrared camera 16. In the situation shown in FIG. 2, which shows the signature (characteristic intensity distribution) 36 in the form of a plurality of rectangular fields arranged in a matrix-like (checkered) manner exclusively in the sense of the possibility of a simple representation, the signature 36 encloses an image area of the IR window 22. This image area is called the measuring location image area 38 corresponding to the function of the IR window 22 as the definition of the measuring location 32 on the body. The digital image 34 comprises the signature 36 and the measuring location image area 38, which is enclosed in the example being shown, in a basically optional manner, by the signature 36. The intensity distribution in the infrared range, which distribution is recorded in the measuring location image area 38, is analyzed for the temperature measurement. This position of the measuring location image area 38 is obtained, for example, based on implicit location information. Implicit location information is, for example, the information that the measuring location image area 38 is located in the center of the signature 36. The corner points or individual corner points of the signature 36 are then determined, for example, in the digital image 34, and the position of the measuring location image area 38 is obtained from this and the implicit location information. The location information may just as well be present as explicit location information and describe the position of the measuring location image area 38 in the form of, for example, an offset vector 40. A position vector 40, which points towards a measuring location image area 38 located in the center of the signature 36, is shown as an example in the view shown in FIG. 2. The position vector 40 may just as well point to a measuring location image area 38 in any other location within the signature 36. In addition, the position vector 40 may also point to a measuring location image area 38 that is located outside the signature 36 and is located at a distance from the signature 36.

The signature 36 or the signature 36 together with location information linked with it makes possible the automatic determination of the position of the measuring location image area 38, namely, of the position in which the measuring location 32 on the body is imaged in the digital image 34. As will be explained below, an automatic determination of the measuring location image area 38 is also possible independently from minor changes in the position of the patient 10 by the analysis of the digital image 34 and the determination of the position of the signature 36 comprised by the digital image 34.

Figure 3A:
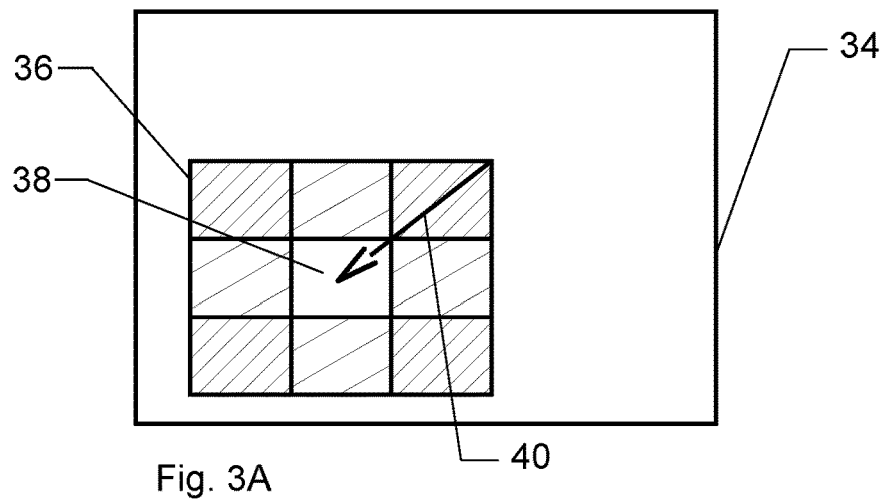
FIGS. 3A to 3C are schematic views showing the signature from FIG. 2 in different positions in a digital image.
Figure 3B:
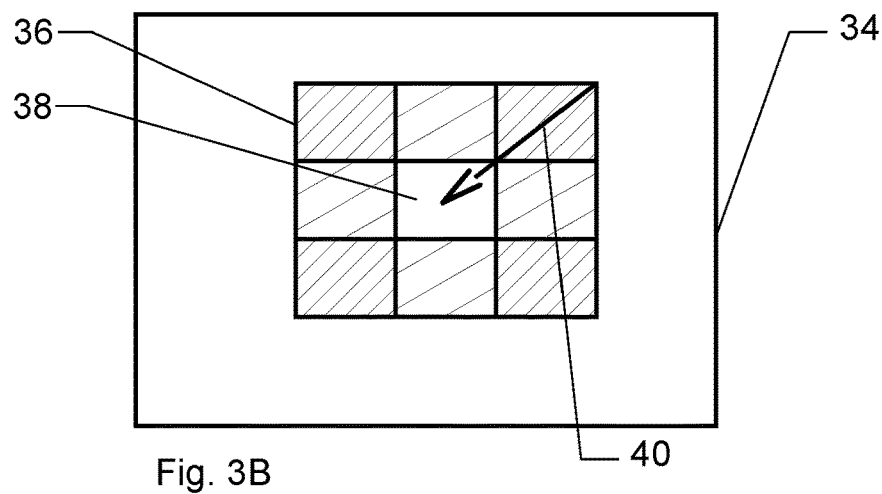
Figure 3C:
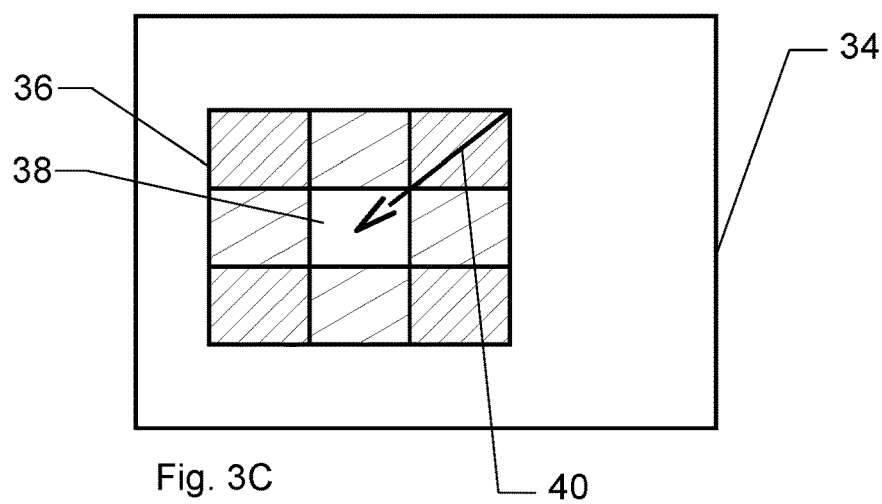
Figure 4A:
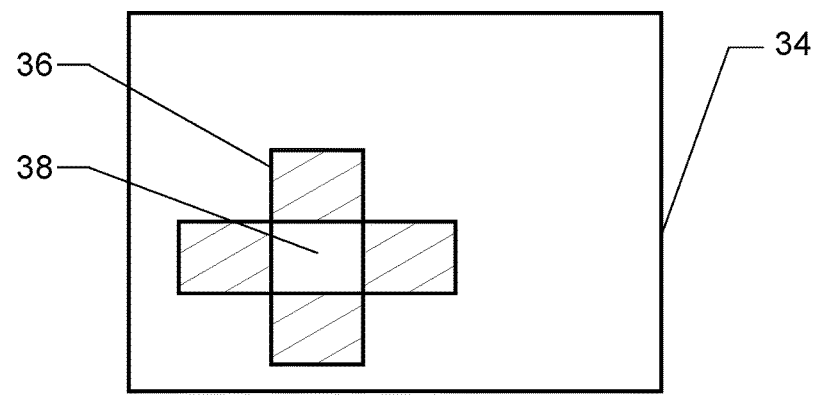
FIGS. 4A to 4F are schematic views showing different signatures of the type shown in FIG. 2.
Figure 4B:
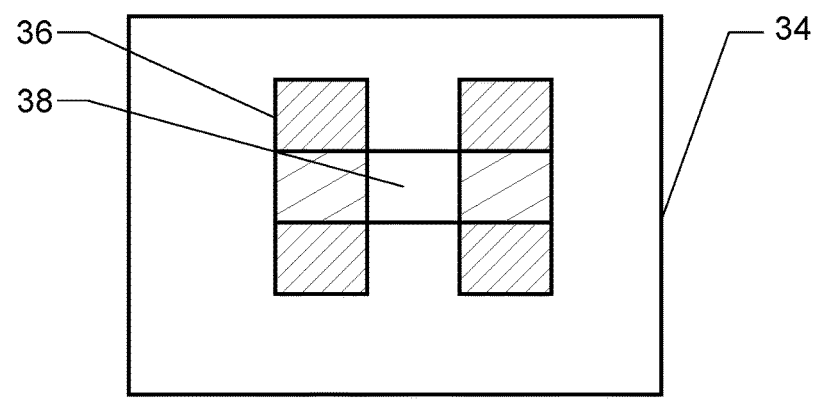
Figure 4C:
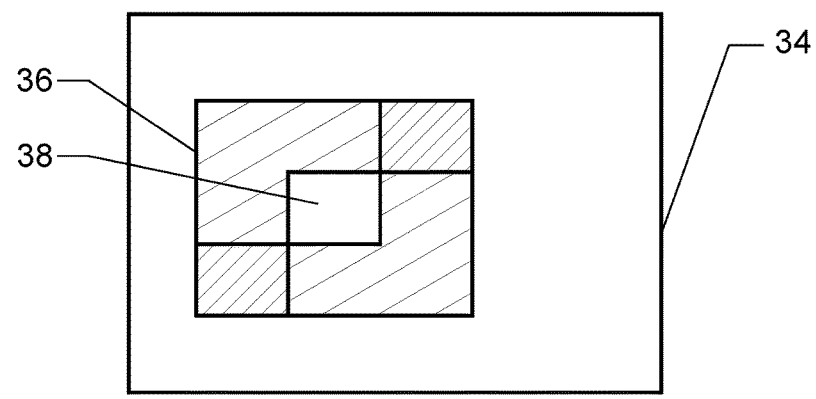
Figure 4D:
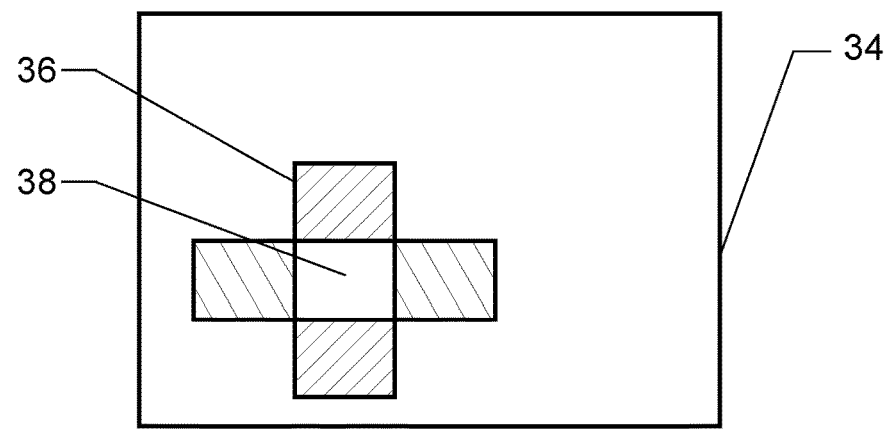
Figure 4E:
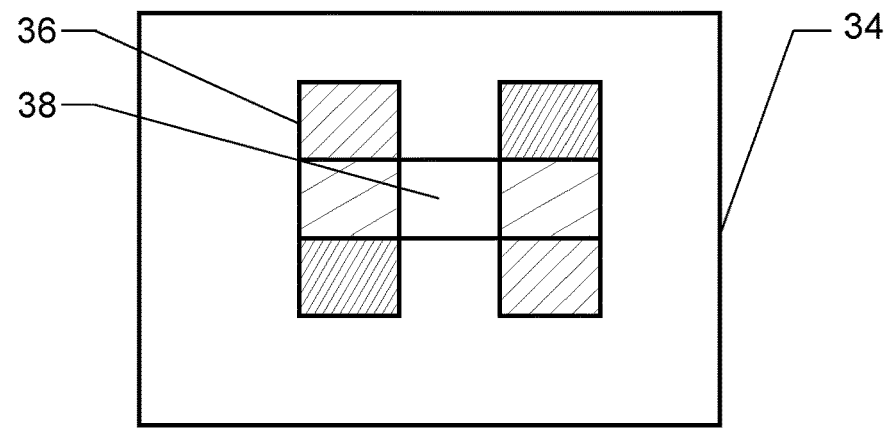
Figure 4F:
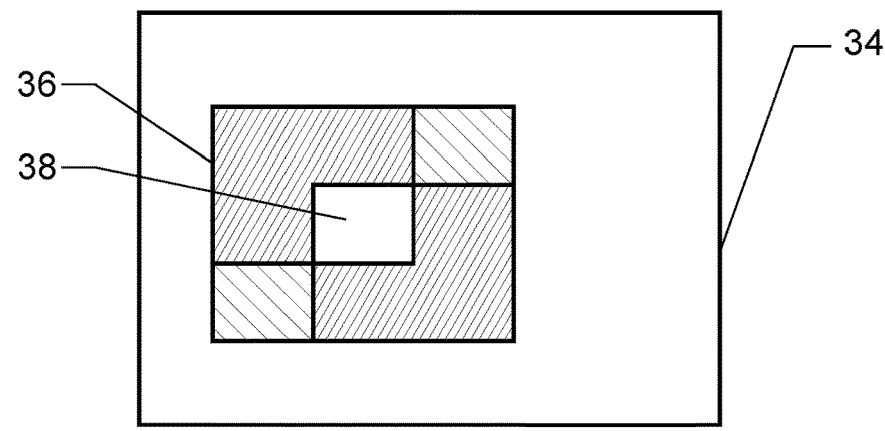

The views in FIG. 3 (FIGS. 3A, 3B, 3C) show that the position of the measuring location image area 38 comprised by the digital image 34 in a particular recorded digital image 34 can be determined easily and reliably. It is necessary for this that the signature 36 be able to be detected automatically (this is possible by means of usual image processing algorithms) and be automatically detected during the operation. A distance in space is also set with the shape of the signature carrier 30 between the parts or sections of the signature carrier 30, which parts or sections act as the origin of the signature 36. This distance belongs to the signature 36 as implicit location information or in the form of explicit location information (e.g., offset vector 40) and must also be found in the digital image 34 and depends, among other things, on the position and the (essentially constant) distance between the (especially stationary) infrared camera 16 and the patient 10. The expected distance between the signature 36 and the measuring location image area 38 is thus likewise known at least more or less and the position of the measuring location image area 38 in the digital image 34 can thus correspondingly be determined automatically with a signature 36 detected in the digital image 34 and with a determination of the position thereof on the basis of the location information belonging to the signature 36, and, for example, the measuring location image area 38 can be extracted from the digital image 34. The distance is possibly distorted based on the perspective of the infrared camera 16. Such a distortion can be calculated, in principle, by means of trigonometric relationships, which are known, in principle, per se in the case of a known camera position/orientation. In case of processes that are based on machine learning, exemplary images from such different perspectives are loaded into the computer program in order also to condition the process to such perspectives and the view following therefrom in the two-dimensional image.

The views shown in FIG. 3 also show that the position of the signature 36 (and of the measuring location image area 38) changes in the digital image 34 in case of minor changes in the position of the patient 10 (the patient 10 is, for example, continuously in the supine position, but is moving on the support 12). In reality, the pattern of the signature 36 is usually additionally distorted depending on the position of the patient 10. The device intended for detecting the skin temperature of the patient 10 is able to a certain extent, by means of the signature 36 marking the measuring location image area 38, to follow minor changes in the position of the patient 10 in the detection area of the infrared camera 16.

Based on the schematically simplified view in FIG. 2 and the signature 36 shown there, it can immediately be seen that different signatures 36 can automatically be distinguished from one another. The view in FIG. 4 (FIGS. 4A through 4F) thus show as an example additional signatures 36 different from the signature 36 in FIG. 2 and that in FIG. 3. The signatures 36 differ by different emissivity distributions in the situation being shown and lead to different intensity distributions despite homogeneous signature carrier temperature in a digital image 34 recorded for a signature carrier 30 with a particular signature 36. The different emissivity distributions and the resulting intensity distributions are illustrated in the views by different shadings. In addition or as an alternative, a signature 36 may also comprise other geometric areas, geometric areas of different sizes, etc. Furthermore, it is not necessary for the measuring location image area 38 to be located in the center of the signature 36. It is only necessary that the spatial relationship of the signature 36 or the signatures and the measuring location image area 38 in relation to one another (for example, distance in the x and y directions from the center/focal point or from a corner point of the signature 36) be known.

The signature 36 is the result of a recording of a digital image 34 in the infrared range for the particular signature carrier 30. The signature carrier 30 comprises areas with different emission and/or transmission characteristics in the infrared range—and hence at least indirectly the signature 36 itself—and these areas are distributed in a characteristic manner over the signature carrier 30, at any rate over at least a part of the signature carrier 30. In the situation shown as an example in a simplified manner in FIG. 2, FIG. 3 and FIG. 4, the cap 20 acting as a signature carrier 30 comprises mutually adjoining areas with different emission and/or transmission characteristics in the infrared range, which areas are rectangular or appear to be rectangular at least in the digital image 34.

The detection of precisely one signature 36 in a digital image 34 recorded by means of the infrared camera 16 makes it possible to infer the orientation of the signature carrier 30 relative to the stationary infrared camera 16. If the signature carrier 30 being worn by the patient 10 has areas with different emission and/or transmission characteristics in the infrared range on different area sections in the manner outlined above, which characteristics lead to at least two different signatures 36 during a recording by means of the infrared camera 16, it is automatically possible to determine the position of the patient 10 on the basis of the respective detected signature 36 (or even based on the circumstance that no signature 36 is possibly detected). As an alternative to a signature carrier 30 comprising at least two signatures 36, it is also possible to use a plurality of signature carriers 30, which the patient carries in respective different locations and which generate at least one signature 36 each. For example, a forehead region, a region of the crown of the head, a temporal region and/or an occipital region of the patient 10 are marked in an automatically analyzable form with both possibilities (one signature carrier 30 with at least two signatures 36; at least two signature carriers 30 with at least one signature 36 each). For example, the position of the patient 10 (supine position, lateral position, prone position) can automatically be determined or at least essentially determined by analyzing the respective recorded digital image 34 and detection of a signature 36 contained therein. A measuring location image area 38 marked by the respective signature 36 can likewise be determined automatically and a temperature measured value can be determined in relation to the measuring location image area 38.

Figure 5:
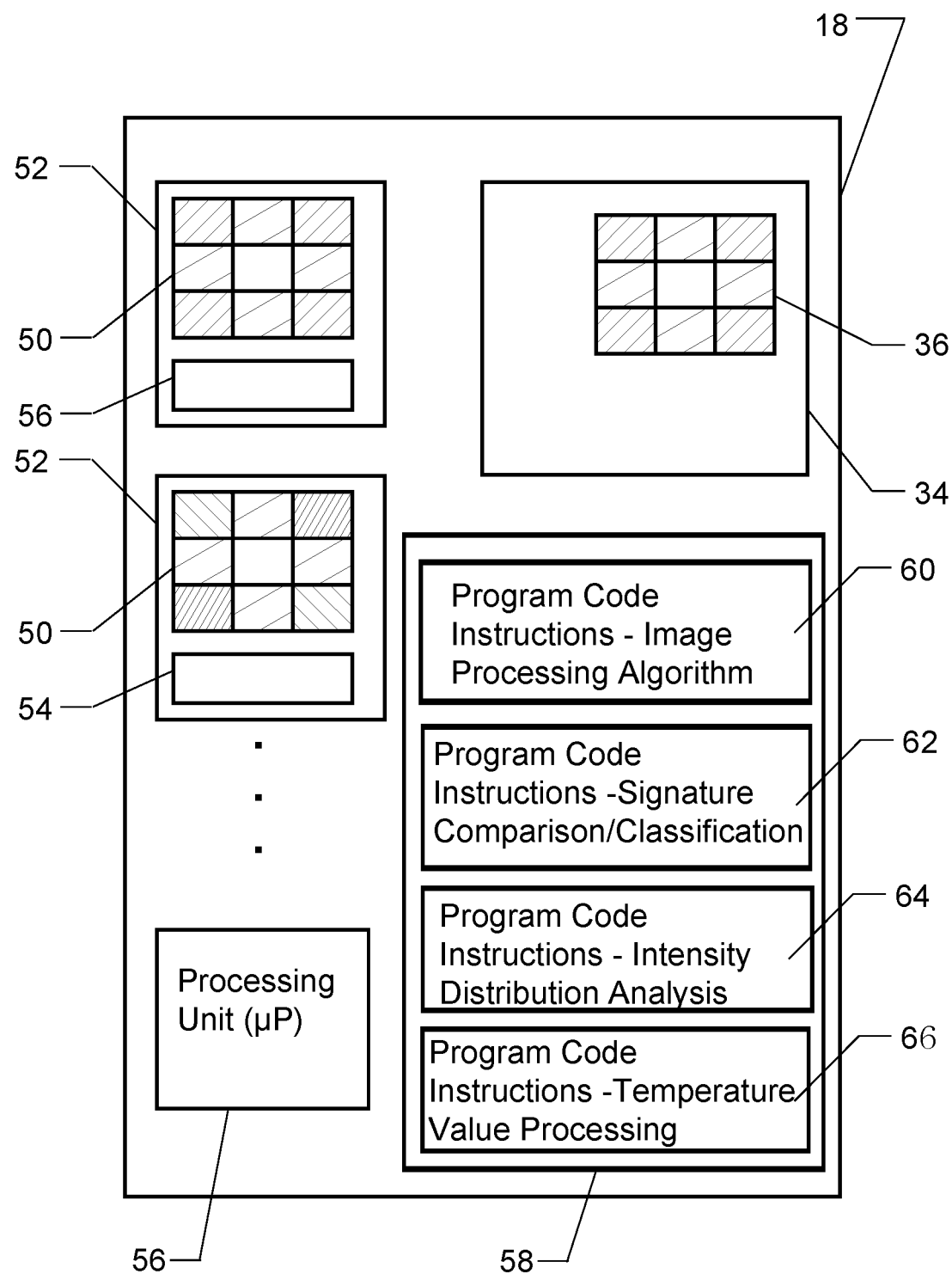
FIG. 5 is a schematic view showing features related to the processing of a signature detected during the recording of a digital image of a patient.

The view in FIG. 5 illustrates the detection and the analysis of a signature 36. The detection of a signature 36 in a digital image 34 recorded by means of the infrared camera 16 is carried out in a manner known, in principle, per se, for example, by an image area that can be considered to be a possible signature 36 being compared with a reference signature 50 being stored in a memory. A signature 36 is detected in case of agreement or sufficient agreement. Location information, for example, an offset vector 40, which was hitherto described as belonging to the signature 36 and codes a position of the measuring location image area 38 relative to the signature 36, may also belong to the reference signature 50 or to each reference signature 50 or respective location information may belong to a respective reference signature 50.

If a plurality of reference signatures 50 are stored in the memory or, in case of the use of machine learning processes, a plurality of classes are established for the different signatures, a comparison is carried out with each reference signature 50 or a classification is performed and a signature 36 is likewise detected in case of an agreement or a sufficient agreement with a reference signature 50. Each reference signature 50 is optionally linked with additional data, which determine the subsequent determination of a temperature measured value, for example, by a defined form of the analysis of the intensity distribution comprised by the measuring location image area 38 being preset.

The contents of a memory, for example, of a memory of the analysis unit 18, with reference signatures 50 stored therein are shown on the left-hand side of the view shown in FIG. 5. A digital image 34 with a signature 36 enclosed thereby, which image was recorded by means of the infrared camera 16, is shown on the right-hand side. The digital image 34 is sent from the infrared camera 16 via the data line 24 into the memory and is available there for analyses and a comparison with the reference signature 50 or reference signatures 50 being stored in the memory. Each reference signature 50 is part of a data set 52, and each data set 52 optionally comprises processing instructions or processing parameters 54 in addition to the reference signature 50. These processing instructions or processing parameters 54 comprise, for example, a coding of an "offset" of the measuring location image area 38 relative to the signature 36 and/or a coding of a position of the patient 10, which can be expected when the digital image 34 comprises a signature 36 corresponding to the respective reference signature 50. As an alternative or in addition, the processing instructions 54 or processing parameters 54 also comprise data that determine the analysis and/or processing of the intensity distribution comprised by the measuring location image area 38 of the digital image 34. In the simplest case, these data are at least a weighting factor. Such a weighting factor has, for example, the value "1.0" in case of a reference signature 50, whose appearance in the digital image 34 is expected in case of a recording of the forehead region of the patient 10, and a higher value, for example, a value of "1.2," whose appearance in the digital image 34 is expected in case of a recording of the region of the crown of the head of the patient 10, etc.

A processing unit 56 is connected to the capturing element (for example CCD-chip) of the infrared camera 16 an d comprises a calculation and evaluation unit (µC, µP, DSP, . . . ), combined with a database or memory unit (RAM, ROM, EEPROM). FIG. 5 shows the processing unit 56 in the form of or in the manner of a microprocessor (µP) as well as a control program 58 loaded into the memory and executable by means of the processing unit 56 are used as means for carrying out the described comparison of a digital image 34 or of a section of a digital image 34 with a signature 36 with at least one reference signature 50. The control program 58 comprises, in a manner known, in principle, per se, program code instructions 60, which code, for example, an image processing algorithm. The image algorithm compares a pattern of pixels of a digital image 34 recorded by of the camera 16, in a matrix system or vector system format, to a predefined pattern (reference signature 50) stored in the matrix system or vector system format and corresponding to a cap structure or other predefined signature carrier structure, to detect a correlation. Such an image processing algorithm makes it possible to detect a signature 36 in a digital image 34 recorded by means of the infrared camera 16. Program code instructions 62, make possible both the comparison and/or a classification of a signature 36 detected in a digital image 34 with at least one reference signature 50. Program code instructions 64 make possible an analysis of an intensity distribution comprised by the measuring location image area 38 of the digital image 34, for determining a temperature value. Program code instructions 66 make possible the application of the processing instruction or instructions 54 or processing parameters 54 to the temperature value. The procedure may comprise the step a) capturing a plurality of infrared images, each containing a plurality of image elements (pixels) produced by the IR camera—the plurality of pixels depending on the resolution of the capturing element and the number of the plurality of images depending on sampling rate and/or the data transfer rate of the camera system. This is followed by the step b) comparing the captured image (for example region by region or pixel by pixel) with a predetermined structure or pattern which corresponds to or is related to a characteristic, for example a signature carrier structure or pattern of an article of clothing (cap), worn on the head of the infant. This predetermined structure may be stored in a matrix, vector, table or similar format. This is followed by step c) determining the position of the infants head or the infant based on the comparison in step b). For example the correlation or pattern recognition is accomplished following one of the known recognition techniques (pattern recognition, skin recognition, object recognition, . . . ) disclosed in U.S. Pat. No. 9,823,755; US 2018 249095; US 2018 004355; US 2015 01189; U.S. Pat. Nos. 9,993,733; 8,831,295; and 9,098,908 (U.S. Pat. No. 9,823,755; US 2018 249095; US 2018 004355; US 2015 01189; U.S. Pat. Nos. 9,993,733; 8,831,295; and 9,098,908 are incorporated herein by reference in their entirety). This is followed by step d) determining a region on the infants head or on the infants body based on the comparison (determined in step c), which is (physiologically) useful for making a regional infrared surface temperature measurement (skin temperature). The steps c) and d) relate to determining the measuring location image area 38. There may be a predefined relationship between the location of the signature (the location of the recognized pattern) and the measuring location image area 38. The processing unit 56, in cooperation with the memory, may be provided with the measuring location image area 38, based on the location of the signature 36, with the predefined relationship determined based on the signature carrier (cap) 30 worn by the infant. With the example of the cap as the signature carrier 30, the cap provides an opening 22 that, when placed on the head of the infant, provides the signature 36 in a digital image 34 and also delimits the measuring location image area 38. This achieves the results for steps c) and d) and particularly results in a determination of the position of the infrared range signature 36 in the digital image 34 to provide signature location information and a determination of a position of the image area 38 of the measuring location on the body in the digital image 34 based on the infrared range signature location information. The procedure continues with e) determining a temperature value or distribution of temperatures on the infants head or the infants body at regions (determined in step d). The procedure advantageously continues with f) (optional) controlling an incubator based on the temperatures (determined in step e). The incubator temperature control advantageously follows one of the known incubator temperature controlling procedures disclosed in U.S. Pat. Nos. 5,316,542; 6,409,653; and 6,048,304 (U.S. Pat. Nos. 5,316,542; 6,409,653; and 6,048,304 are incorporated herein by reference in their entirety).

Individual aspects of the specification being filed here can thus be briefly summarized as follows: a key aspect of the invention being presented here is the application of a signature carrier 30 to provide a signature 36 for marking or indicating a measuring location on the body (measuring area on the area) 32 in a digital image 34. Another, optional aspect of the invention being presented here is the application of distinguishable signatures 36 for the distinguishable marking of different measuring locations 32 on the body in a digital image 34. The patient 10 himself/herself carries the origin of the respective signature 36, namely, the signature carrier 30. The signature carrier 30 advantageously comprises a body wearable portion, for example, a cap 20 acting as a signature carrier 30. A signature 36 indicating a measuring location 32 on the body is detected by means of a sensor system 16 in the process being presented here for the contactless determination of a measuring location 32 on the body, which measuring location is intended for the measurement of a skin temperature of a human being 10, and for the subsequent determination of the skin temperature, and the skin temperature measurement is carried out at the detected measuring location 32 on the body. The process is characterized in that a signature 36 detectable in the infrared range as well as a sensor system 16 sensitive in the infrared range are used, and both the detection of the signature 36 and the measurement of the skin temperature on the measuring location 32 on the body are carried out by means of the sensor system 16 sensitive in the infrared range.

While specific embodiments of the invention have been shown and described in detail to illustrate the application of the principles of the invention, it will be understood that the invention may be embodied otherwise without departing from such principles.

APPENDIX

List of Reference Designations

10 Patient
12 Support
14 Treatment unit, incubator
16 Infrared camera
18 Analysis unit
20 Article of clothing, cap
22 Opening, IR window
24 Data line
26 Temperature signal
28 Display unit
30 Signature carrier
32 Measuring point on the body 34 Digital image
36 Signature
38 Measuring point image area
40 Offset vector (location information)
50 Reference signature
52 Data set
54 Processing instruction or processing parameter
56 Processing unit
58 Control program
60 Program code instructions
62 Program code instructions
64 Program code instructions
66 Program code instructions

What is claimed is:

1. A process for a contactless determination of a measuring location on a body of a human being, which measuring location is intended for a measurement of a skin temperature of the human being, the process comprising the steps of:
providing an infrared range sensitive sensor system;
detecting an infrared range signature indicating the measuring location on the body with the infrared range sensitive sensor;
carrying out a skin temperature measurement on the measuring location on the body with the infrared range sensitive sensor;
providing an infrared camera as the infrared range sensitive sensor;
recording a digital image comprising at least a part of the human being as well as the infrared range signature with the infrared camera;
determining a position of the infrared range signature in the digital image to provide signature location information;
determining a position of an image area of the measuring location on the body in the digital image based on the infrared range signature location information;
determining a skin temperature of the human being by analyzing a radiation intensity distribution, in the infrared range, in the image area of the measuring location, wherein analyzing a radiation intensity distribution comprises the steps of:
identifying the infrared range signature in the digital image;
comparing the identified signature with at least one reference signature; and
determining the skin temperature corresponding to a processing parameter linked with a reference signature fitting the infrared range signature and/or corresponding to a processing instruction linked with the reference signature fitting the infrared range signature.

2. A process in accordance with claim 1, further comprising providing a signature carrier on the human being, wherein the infrared range signature is defined by the signature carrier.

3. A process in accordance with claim 2, wherein an article of clothing being worn by the human being comprises the infrared range signature and acts as the signature carrier.

4. A process in accordance with claim 2, wherein a film is applied detachably to the skin of the human being and the film comprises the infrared range signature and acts as the signature carrier.

5. A process in accordance with claim 2, wherein the infrared range signature carrier comprises at least two area sections with different emission, transmission or reflection characteristics in the infrared range.

6. A process in accordance with claim 2, wherein the infrared range signature carrier has at least one infrared transparent opening defining the measuring location.

7. A process in accordance with claim 2, wherein the skin temperature measurement is carried out as a function of the detected signature.

8. A process in accordance with claim 2, wherein the infrared range signature carrier comprises different infrared range signatures in different sections.

9. A process in accordance with claim 1, wherein a computer program with program code carries out the steps of detecting an infrared range signature and carrying out a skin temperature measurement, with said steps executed with a processing unit comprising one or more microprocessor.

10. A process in accordance with claim 1, wherein the processing parameter comprises one of a coding of an offset of the image area of the measuring location relative to the infrared range signature and a coding of a position of the human being.

11. A process in accordance with claim 1, wherein the processing parameter comprises data that determine one or more of analyzing and processing of the radiation intensity distribution comprised by the image area of the measuring location of the digital image.

12. A treatment system for a contactless determination of a measuring location on a body of a human being and for a measurement of a skin temperature of the human being, the treatment system comprising:
a treatment unit comprising an infrared range sensitive sensor system and a processing unit cooperating with the infrared range sensitive sensor system for detecting an infrared range signature indicating a measuring location on the body with the infrared range sensitive sensor and carrying out a skin temperature measurement on the measuring location on the body with the infrared range sensitive sensor, the infrared range sensitive sensor system comprising an infrared camera, the processing unit comprising one or more microprocessor and the processing unit being provided with program code to detect the infrared range signature and carry out the skin temperature measurement, wherein the processing unit is configured to record a digital image comprising at least a part of the human being as well as the infrared range signature with the infrared camera, determine a position of the infrared range signature in the digital image to provide signature location information, determine a position of an image area of the measuring location on the body in the digital image based on the infrared range signature location information and determine a skin temperature of the human being by analyzing a radiation intensity distribution, in the infrared range, in the image area of the measuring location, wherein the processing unit analyzes a radiation intensity distribution by identifying the infrared range signature in the digital image, comparing the identified signature with reference signatures and determines the skin temperature corresponding to a processing parameter linked with one of the reference signatures that best fits the infrared range signature and/or corresponding to a processing instruction linked with the reference signature that best fits the infrared range signature.

13. A treatment system in accordance with claim 12, further comprising a signature carrier provided on the human being, wherein:

the infrared range signature is carried by the signature carrier;

the signature carrier has at least one infrared transparent opening defining the measuring location; and the signature carrier defines the signature with a known shape and size and defines the measuring location with a predetermined position relative to the signature.

14. A treatment system in accordance with claim 13, wherein an article of clothing defines the signature carrier and comprises at least two area sections having different emission, transmission or reflection characteristics with the known shape and size.

15. A treatment system in accordance with claim 12, wherein the processing parameter comprises one of a coding of an offset of the image area of the measuring location relative to the infrared range signature and a coding of a position of the human being.

16. A treatment system in accordance with claim 12, wherein the processing parameter comprises data that determine one or more of analyzing and processing of the radiation intensity distribution comprised by the image area of the measuring location of the digital image.

17. An article of clothing for a treatment system for a contactless determination of a measuring location on a body of a human being and for a measurement of a skin temperature of the human being, the article of clothing comprising:

a body wearable portion with a first area section and a second are section wherein the first area section and the second are section have different emission, transmission or reflection characteristics to define a signature with a known shape and size and define a measuring location with a predetermined position relative to the signature, the infrared range sensitive sensor system further comprises a treatment unit comprising an infrared range sensitive sensor system and a processing unit cooperating with the infrared range sensitive sensor system for detecting an infrared range signature indicating a measuring location on the body with the infrared range sensitive sensor and carrying out a skin temperature measurement on the measuring location on the body with the infrared range sensitive sensor, the infrared range sensitive sensor system comprising an infrared camera, the processing unit comprising one or more microprocessor and is provided with program code to detect the infrared range signature and carry out the skin temperature measurement, the processing unit being configured to record a digital image comprising at least a part of the human being as well as the infrared range signature with the infrared camera, determine a position of the infrared range signature in the digital image to provide signature location information, determine a position of an image area of the measuring location on the body in the digital image based on the infrared range signature location information and determine a skin temperature of the human being by analyzing a radiation intensity distribution, in the infrared range, in the image area of the measuring location, the processing unit analyzing a radiation intensity distribution by identifying the infrared range signature in the digital image, comparing the identified signature with reference signatures and determines the skin temperature corresponding to a processing parameter linked with one of the reference signatures that best fits the infrared range signature and/or corresponding to a processing instruction linked with the reference signature that best fits the infrared range signature.

18. An article of clothing according to claim 17, wherein: the body wearable portion comprises a cap as a part of the treatment system.

19. An article of clothing according to claim 17, wherein the processing parameter comprises one of a coding of an offset of the image area of the measuring location relative to the infrared range signature and a coding of a position of the human being.

20. An article of clothing according to claim 17, wherein the processing parameter comprises data that determine one or more of analyzing and processing of the radiation intensity distribution comprised by the image area of the measuring location of the digital image.

* * * * *